(12) United States Patent
Huang

(10) Patent No.: US 11,141,171 B2
(45) Date of Patent: Oct. 12, 2021

(54) BONE DRILLING COVER FIXING DEVICE

(71) Applicant: OSSAWARE BIOTECH CO., LTD., Changhua County (TW)

(72) Inventor: Max Huang, Changhua County (TW)

(73) Assignee: OSSAWARE BIOTECH CO., LTD., Changhua County (TW)

( * ) Notice: Subject to any disclaimer, the term of this patent is extended or adjusted under 35 U.S.C. 154(b) by 176 days.

(21) Appl. No.: 16/558,157

(22) Filed: Sep. 2, 2019

(65) Prior Publication Data
US 2021/0059690 A1 Mar. 4, 2021

(51) Int. Cl.
*A61B 17/16* (2006.01)
*A61B 17/00* (2006.01)

(52) U.S. Cl.
CPC ............ *A61B 17/1695* (2013.01); *A61B 2017/00477* (2013.01)

(58) Field of Classification Search
CPC ..... A61B 17/68; A61B 17/88; A61B 17/1633; A61B 17/1695; A61B 17/688; A61B 2017/00477; A61B 17/8875
See application file for complete search history.

(56) References Cited

U.S. PATENT DOCUMENTS

2008/0172097 A1* 7/2008 Lerch .................. A61B 17/688
606/324
2013/0282011 A1* 10/2013 Brogan .............. A61B 17/8872
606/75

FOREIGN PATENT DOCUMENTS

EP        3381388 A2 * 10/2018 ......... A61B 17/8875

* cited by examiner

*Primary Examiner* — George J Ulsh
(74) *Attorney, Agent, or Firm* — Leong C. Lei

(57) ABSTRACT

A bone drilling cover fixing device includes an upper fastening member and a lower fastening member. The upper fastening member includes a first base portion and a first coupling portion. The first coupling portion protrudes from an underside of the first base portion and can be inserted into a drilled hole. The lower fastening member includes a second base portion and a second coupling portion. The second base portion includes at least one first arm and at least one second arm. The first arm has a length equal to that of the second arm. The length of the first arm and the length of the second arm are greater than a radius of the drilled hole. When in use, the first and second arms are inserted in an oblique manner into the drilled hole to be positioned at two ends of an underside of the drilled hole.

9 Claims, 16 Drawing Sheets

BONE DRILLING COVER FIXING DEVICE

FIELD OF THE INVENTION

The present invention relates to a bone drilling cover fixing device, and more particularly to a bone drilling cover fixing device that can be applied to cover a drilled hole of any bone or to fix a cranial bone and that can be widely used and operated with ease. The diameter of the drilled hole is minimized for reducing damage to the bone structure.

BACKGROUND OF THE INVENTION

Taiwan Patent Publication No. 1609670 discloses a cranial bone fixing device and a surgical tool thereof, owned by the applicant. The cranial bone fixing device comprises a lower fastening member and a movable retaining assembly. When the entire movable retaining assembly is positioned by the outer sleeve of the surgical tool, it can be arranged at a certain distance from the outer surface of the cranium to facilitate implantation and restoration of the cranial bone.

The aforementioned fixing device can provide a convenient and progressive clinical operation for fixing the cranial bone. However, the lower fastening member is a circular structure, and its outer diameter is greater than the inner diameter of the drilled hole, so it can only be used for fixing the original cut cranial bone to the cranium. As to a single drilled hole for the placement of a monitor, probe or drainage tube, because the lower fastening member cannot be inserted into the cranium via the drilled hole, the fixing device cannot be used for covering the drilled hole, and it is necessary to use another object for covering the drilled hole. As a result, the above invention cannot achieve the purpose of fixing the cranial bone and covering the drilled hole. In addition, if bone grafting is performed, it is necessary to drill a hole in part of the body such as the femur, the hand bone, the foot bone or the sternum; or when the surgical instrument needs to pass through the adjacent bone for surgical operation, it is also necessary to drill a hole in the bone. Similarly, the lower fastening member of the above-mentioned invention cannot be inserted into a single drilled hole, so it is not suitable for covering the single drilled hole. If the drilled hole is not covered to be in a hollow state, the soft and hard tissues are easily filled to affect the normal bone hyperplasia. Besides, if the drilled hole is not covered, it is easily damaged when touched by an external force. This is a problem that the medical staff is trying to solve.

Accordingly, the inventor of the present invention has devoted himself based on his many years of practical experiences to solve these problems.

SUMMARY OF THE INVENTION

The primary object of the present invention is to provide a bone drilling cover fixing device, comprising an upper fastening member and a lower fastening member. The upper fastening member includes a first base portion and a first coupling portion. The first coupling portion is disposed on the first base portion and protrudes from an underside of the first base portion. The first coupling portion has a diameter less than a diameter of a drilled hole. The lower fastening member includes a second base portion and a second coupling portion. The second base portion includes at least one first arm and at least one second arm. The first arm has a length equal to that of the second arm. The second coupling portion is disposed on the second base portion. Each of the length of the first arm and the length of the second arm is greater than a radius of the drilled hole. When in use, the first arm and the second arm are inserted in an oblique manner into the drilled hole to be positioned at two ends of an underside of the drilled hole, the second coupling portion is coupled to the first coupling portion, and a movement caused by a clearance between the first coupling portion and the drilled hole is not sufficient to disengage any one of the first arm and the second arm from the two ends of the underside of the drilled hole.

Preferably, the second base portion is in a platy shape and has a width less than the diameter of the drilled hole.

Preferably, the second coupling portion has an outer cut surface.

Alternatively, the second coupling portion has a plurality of outer cut surfaces.

In the bone drilling cover fixing device provided by the present invention, through the first arm and the second arm having the same length that is slightly greater than the radius of the drilled hole, the lower fastening member is inserted in an oblique manner toward the drilled hole, such that the first arm and the second arm can be smoothly and quickly inserted and positioned to the underside of the drilled hole for covering the drilled hole of any bone. The operation is very quick and easy. The diameter of the drilled hole is minimized for reducing damage to the bone structure. When the invention is used for fixing the cranial bone, the first arm and the second arm are configured to span and hold the cranial bone and the cranium. The invention can be widely used to improve the shortcomings of the prior art.

Embodiments of the present invention will now be described, by way of example only, with reference to the accompanying drawings.

DETAILED DESCRIPTION OF THE PREFERRED EMBODIMENTS

Figure 1:
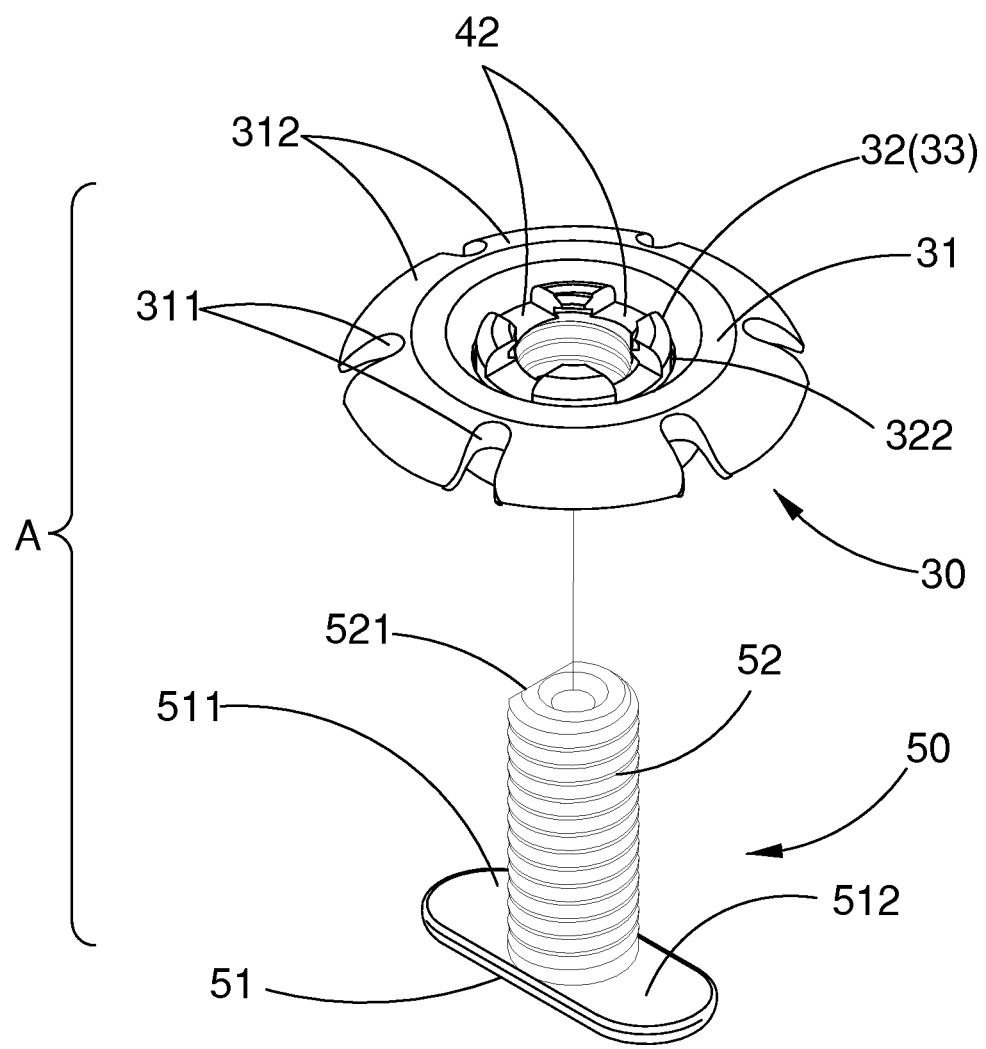
FIG. 1 is a top exploded view of the present invention.
Figure 2:
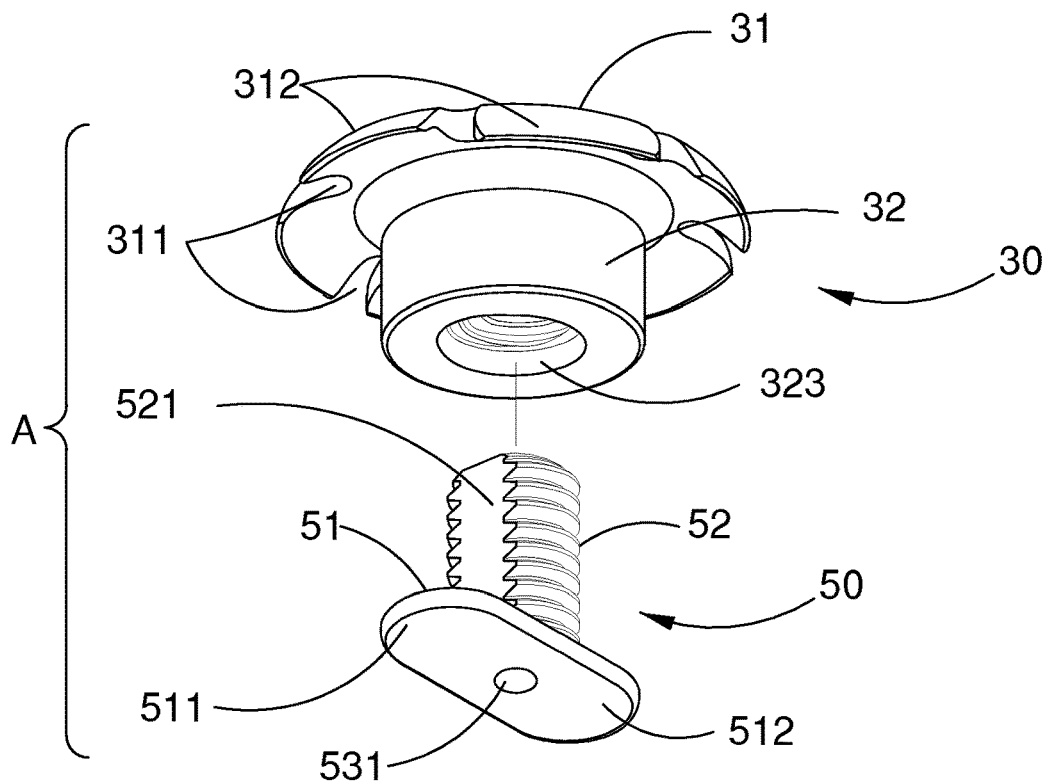
FIG. 2 is a bottom exploded view of the present invention.
Figure 3:
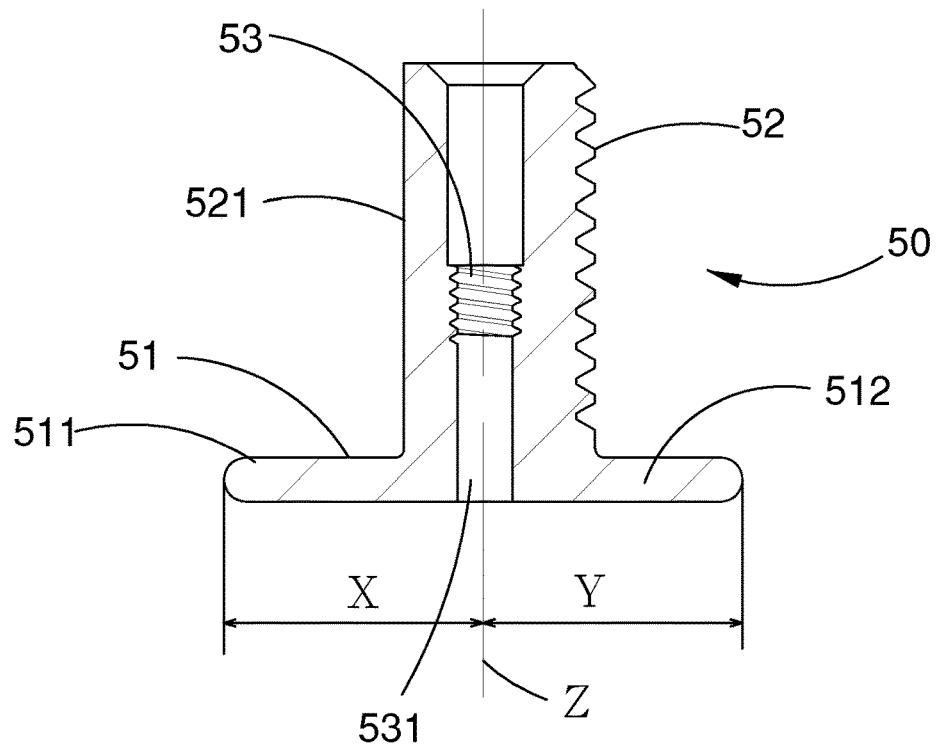
FIG. 3 is a cross-sectional view of the lower fastening member of the present invention.

Referring to FIG. 1 through FIG. 10, the present invention discloses a bone drilling cover fixing device A, comprising an upper fastening member 30 and a lower fastening member 50.

The upper fastening member 30 includes a first base portion 31 and a first coupling portion 32 disposed at the middle of the first base portion 31. The first base portion 31 is in the form of a plate or a disk having an outer circumference that is formed with a plurality of spaced slits 311 to form a plurality of petal-like segments 312. The plurality of petal-like segments 312 each have a thickness that is gradually reduced toward its outer periphery so as to be secured to the cranium 70 easily. The first coupling portion 32 protrudes from the underside of the first base portion 31, and has a diameter D2 slightly less than the diameter D1 of the drilled hole 73 so as to be placed in the drilled hole 73. The first coupling portion 32 is an annular sleeve with a cavity portion 322 having an opening facing upward and a bottom in which a through hole 323 is formed. The through hole 323 is in communication with the cavity portion 322. A nut 33 is disposed in the cavity portion 322. The upper edge of the cavity portion 322 is formed with an engaging groove 321 having a smaller inner diameter. A first positioning portion 42 is disposed on the periphery of the upper end of the nut 33 for connecting a surgical tool B. Preferably, the first positioning portion 42 is a concave-convex configuration annularly formed on the periphery of the upper end of the nut 33 or includes at least two pits (not shown) on the upper end surface of the nut 33. A raised ring 41 having an outer diameter greater than the engaging groove 321 protrudes from a lower edge of an outer peripheral surface of the nut 33, so that the nut 33 can only rotate axially in the cavity portion 322 without departing from the cavity portion 322.

The lower fastening member 50 includes a platy second base portion 51 having a width less than the diameter D1 of the drilled hole 73 and a second coupling portion 52 disposed at the middle of the second base portion 51. The second coupling portion 52 is a screw rod to be screwed to the nut 33. The second coupling portion 52 is formed with an inner screw hole 53 for connecting the surgical tool B. An outer cut surface 521 is disposed on one side of the second coupling portion 52. The outer cut surface 521 is disposed corresponding to one of a first arm 511 and a second arm 512, which facilitates the lower fastening member 50 to be inserted in an oblique manner toward the drilled hole 73. The second base portion 51 includes a first arm 511 and a second arm 512. The first arm 511 has a length equal to that of the second arm 512. The first arm 511 and the second arm 512 are arranged in a line with a center line Z of the second coupling portion 52 (screw rod) as a center. Both the length X of the first arm 511 and the length Y of the second arm 512 are greater than a radius R1 of the drilled hole 73, so that the lower fastening member 50 can be inserted in an oblique manner into the drilled hole 73 to be positioned at two ends of the underside of the drilled hole 73 during the surgical operation. When the second coupling portion 52 is coupled to the first coupling portion 32 to be positioned, the movement caused by the clearance between the first coupling portion 32 and the drilled hole 73 is not sufficient to disengage any one of the first arm 511 and the second arm 512 from the two ends of the underside of the drilled hole 73.

Figure 4:
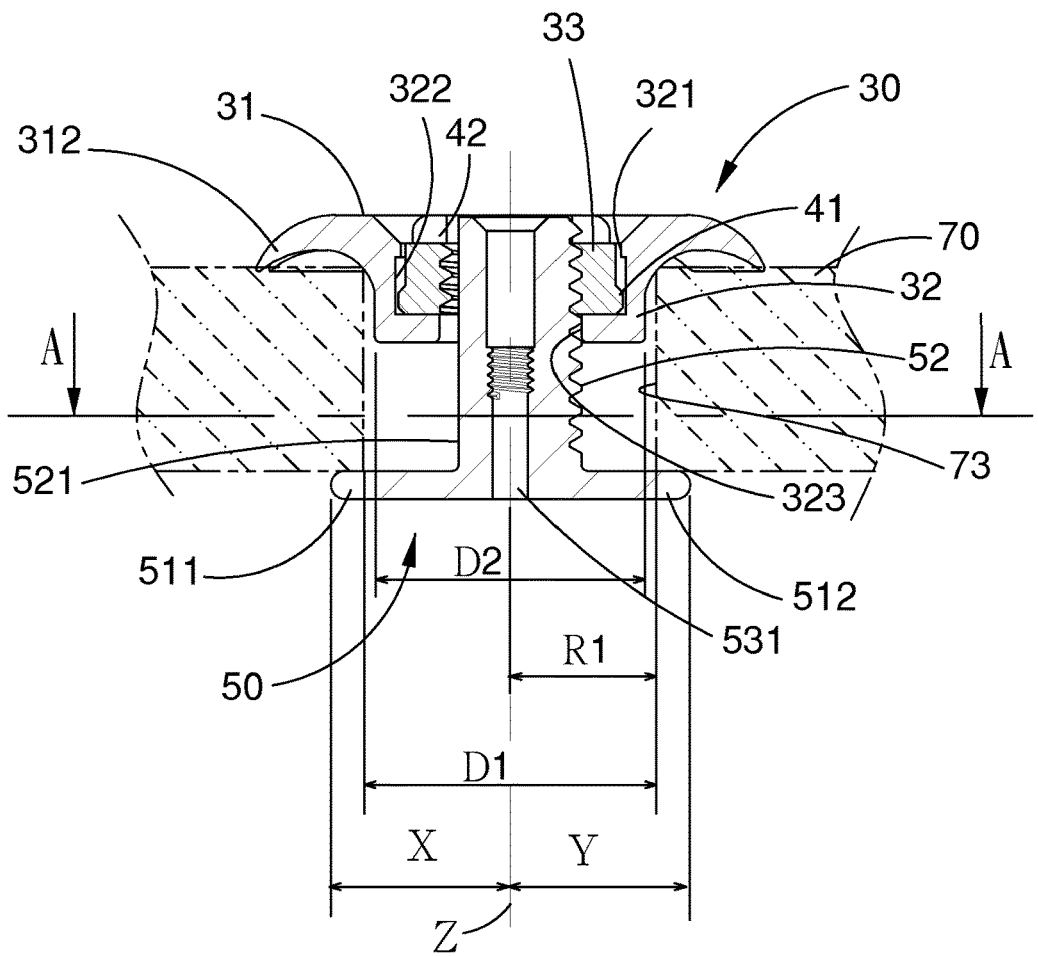
FIG. 4 is a cross-sectional view of the present invention used for covering the drilled hole of the cranial bone.
Figure 5:
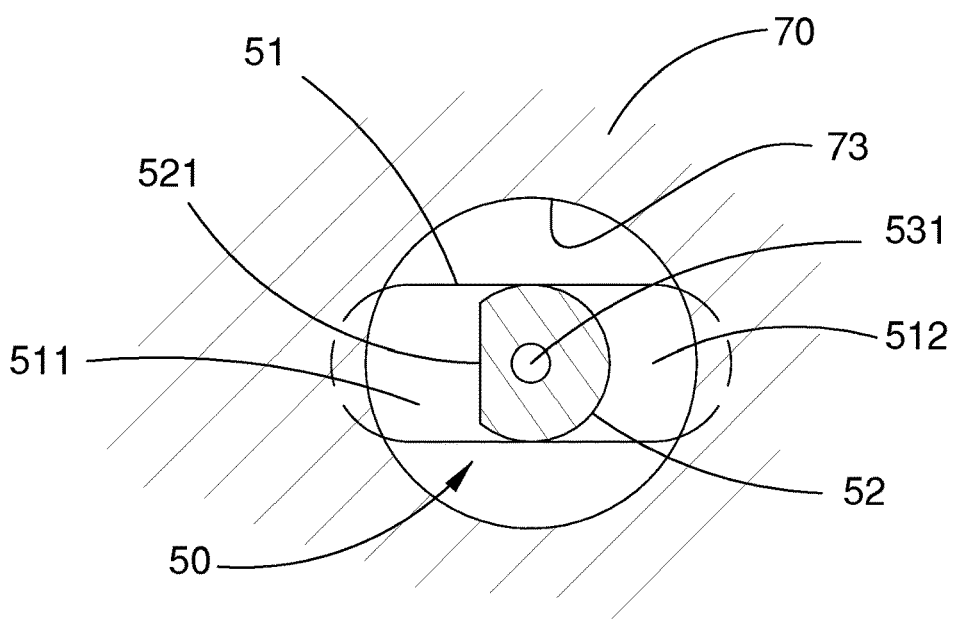
FIG. 5 is a sectional view taken along line A-A of FIG. 4.
Figure 6:
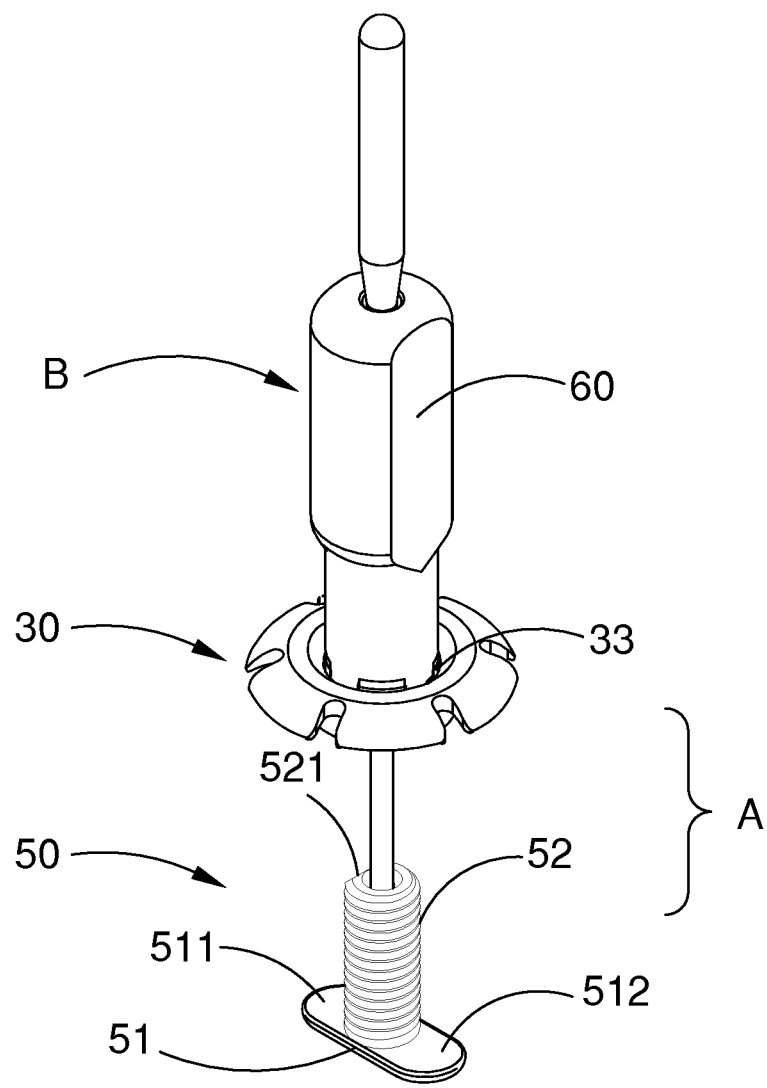
FIG. 6 is a perspective view of the present invention combined with the surgical tool.
Figure 7:
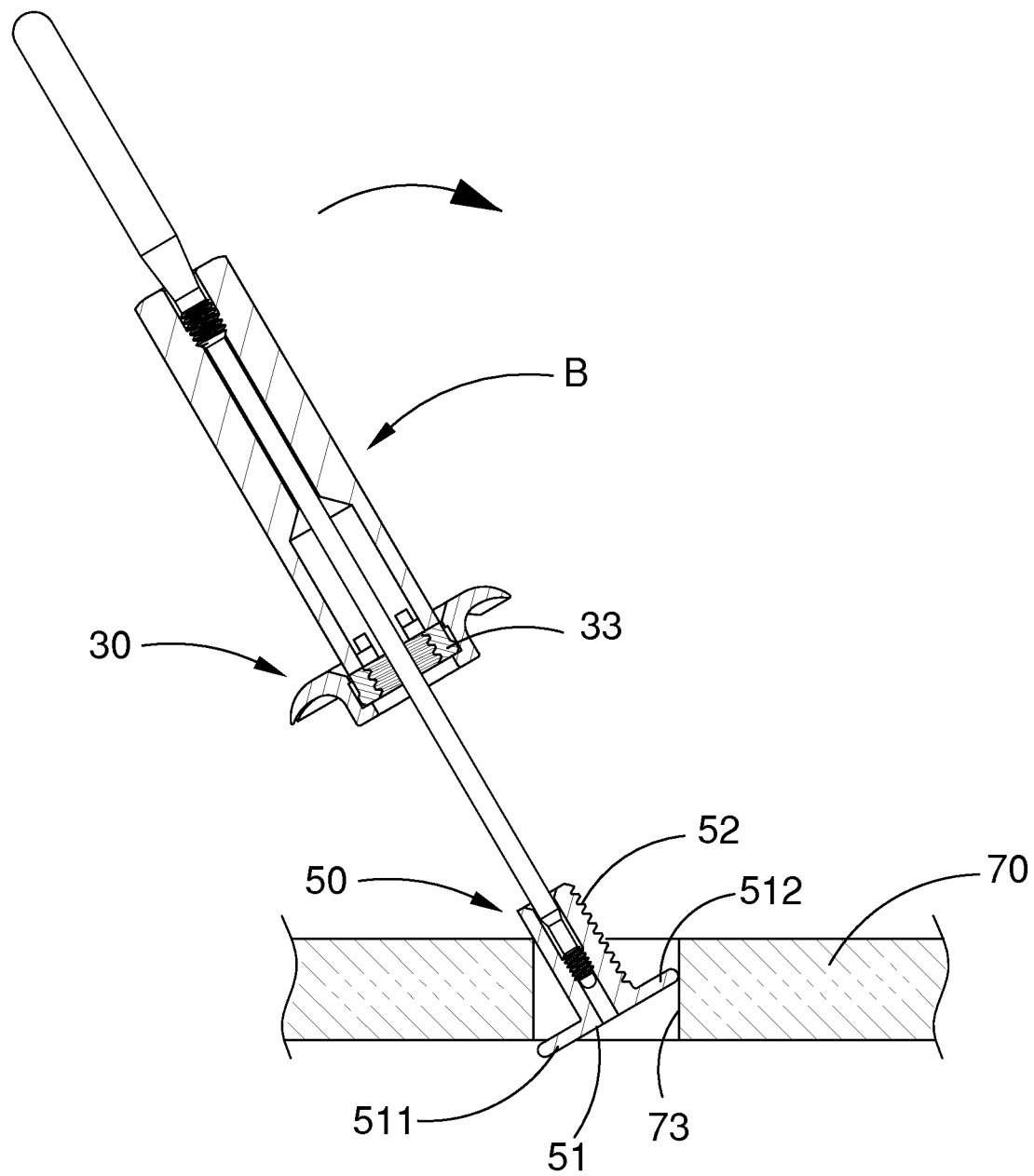
FIG. 7 is a schematic view showing the operation that the lower fastening member is inserted in an oblique manner toward the drilled hole according to the present invention.
Figure 8:
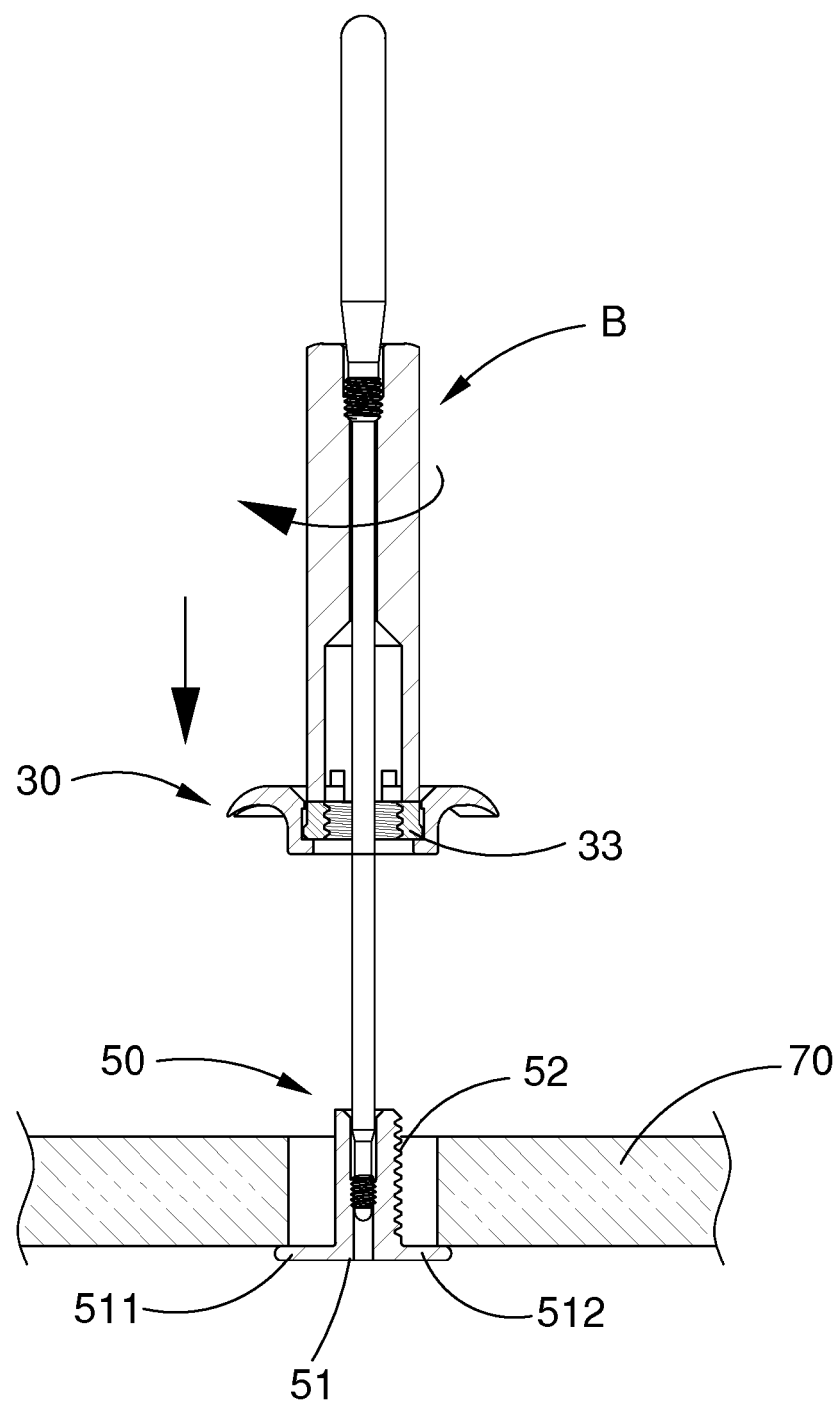
FIG. 8 is a schematic view showing the operation that the first arm and the second arm span the drilled hole to be positioned to the two ends of the underside of the drilled hole according to the present invention.
Figure 9:
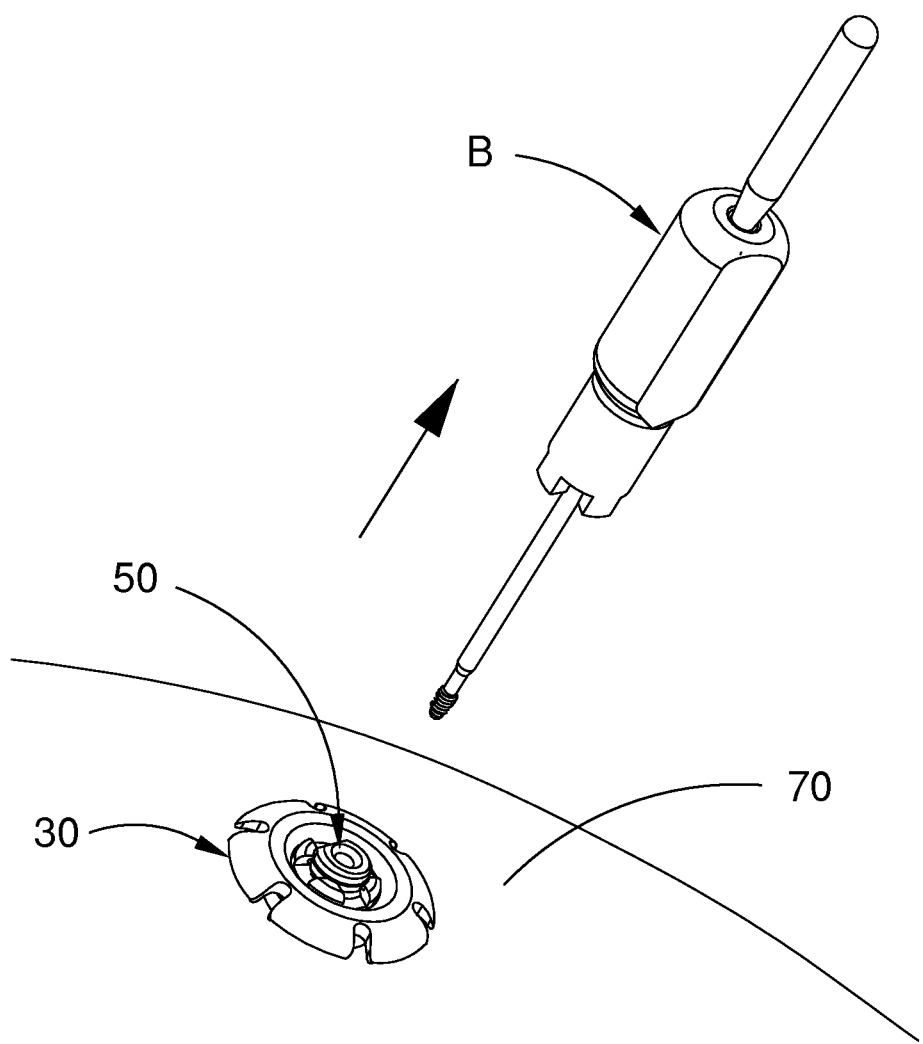
FIG. 9 is a schematic view showing that the surgical tool is pulled out after the upper fastening member and the lower fastening member are fastened to cover the drilled hole according to the present invention.

FIGS. 4 to 9 illustrate the operation of the present invention used for bone drilling. The connecting structure and operation of the present invention and the surgical tool B are similar to the technique as disclosed in Taiwan Patent Publication No. 1609670 filed by the same applicant, and will not be described hereinafter. The bone drilling cover fixing device A of the present invention is first coupled with the surgical tool B to form an integral assembly, as shown in FIG. 6. The second base portion 51 of the lower fastening member 50 is in a platy shape having a proper width. The first arm 511 and the second arm 512 have the same length that is greater than the radius R1 of the drilled hole 73. Therefore, the whole assembly is taken in an oblique manner and the lower fastening member 50 is inserted in an oblique manner toward the drilled hole 73, such that the first arm 511 and the second arm 512 can be smoothly and quickly inserted to the underside of the drilled hole 73 (as shown in FIG. 7) to be positioned at the two opposite sides of the underside of the drilled hole 73 (as shown in FIG. 8). When the upper fastening member 30 is moved downwardly by the surgical tool B to screw the nut 33 downwardly to the second coupling portion 52 (screw rod) of the lower fastening member 50, the nut 33 synchronously drives the upper fastening member 30 to be moved downwardly and tightly positioned with the first arm 511 and the second arm 512, and the upper fastening member 30 covers the drilled hole 73. Finally, the surgical tool B is pulled out, that is, the drilled hole 73 is covered (as shown in FIG. 4 and FIG. 9). The operation is very convenient and fast.

The foregoing is an embodiment of the present invention used for covering a single drilled hole of the cranium. The present invention may be applied to cover a drilled hole of any bone, not limited thereto.

Figure 10:
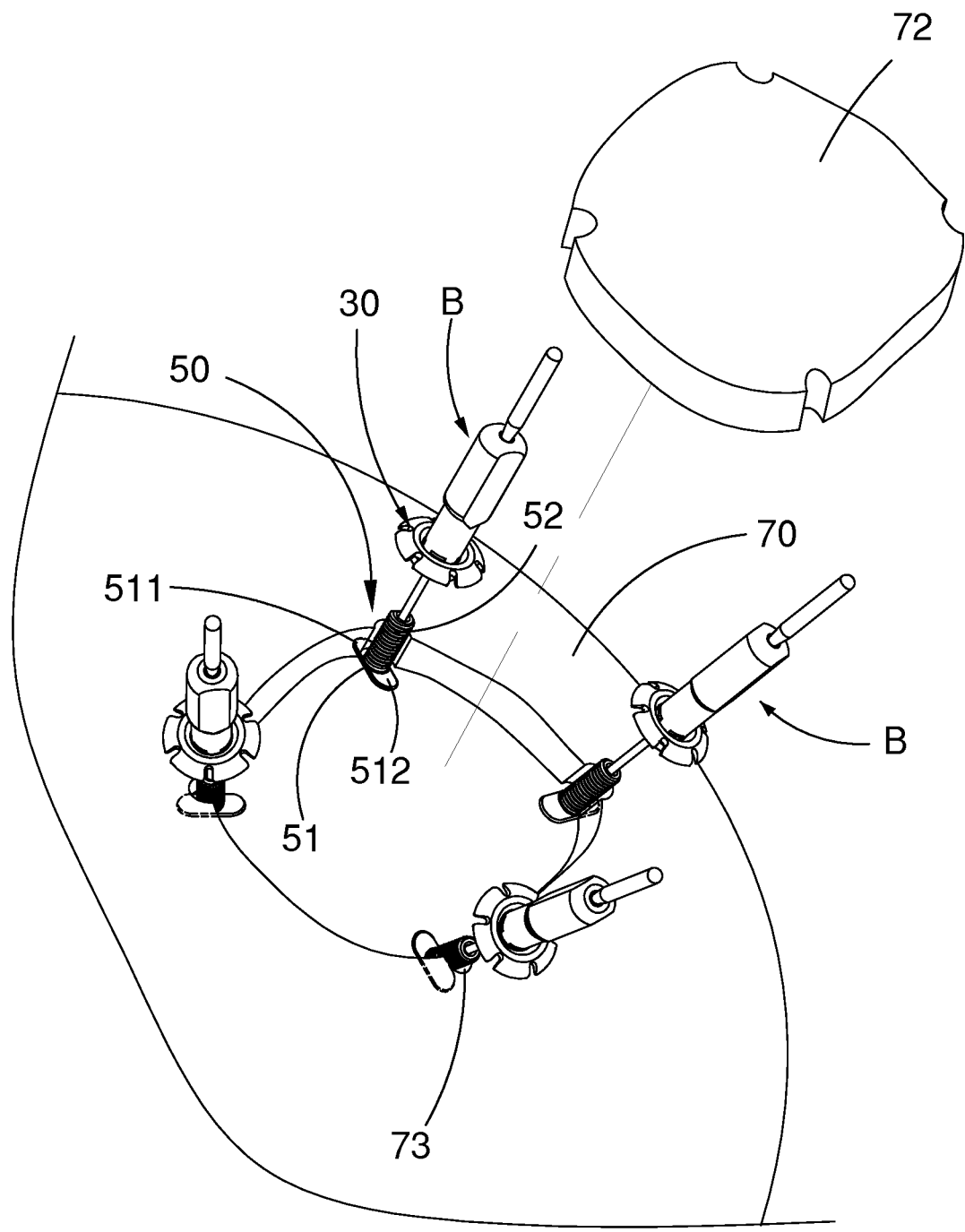
FIG. 10 is a schematic view according to an embodiment of the present invention used for fixing the cranial bone and the cranium.

As shown in FIG. 10, the present invention is used for fixing the cranial bone. The connecting structure and operation of the present invention and the surgical tool B are similar to the technique as disclosed in Taiwan Patent Publication No. 1609670 filed by the same applicant, and will not be described hereinafter. The bone drilling cover fixing device A of the present invention is first coupled with the surgical tool B to form an integral assembly, which facilitates the bone drilling cover fixing device A and the surgical tool B to be directly placed in the drilled hole 73 of the cranium 70 simultaneously. The second base portion 51 of the lower fastening member 50 of the present invention has the first arm 511 and the second arm 512 in the same length to span and hold the cranial bone 72 and the cranium 70. Then, the upper fastening member 30 is moved downwardly by the surgical tool B to screw the nut 33 downwardly to the second coupling portion 52 (screw rod), such that the upper fastening member 30 and the first arm 511 and the second arm 512 of the lower fastening member 50 are driven and fastened to generate a clamping force for fixing the cranial bone 72 to the cranium 70. It is convenient and quick for operation.

Figure 11:
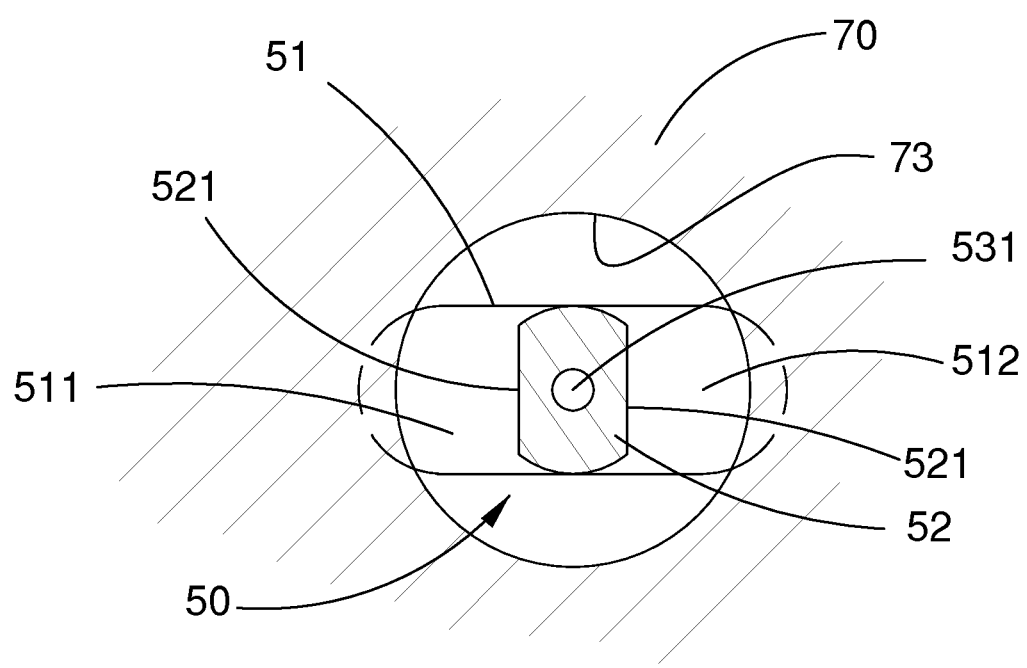
FIG. 11 illustrates a second embodiment of the second coupling portion of the present invention.

FIG. 11 illustrates a second embodiment of the second coupling portion 52 of the present invention. Two opposite sides of the second coupling portion 52 of the lower fastening member 50 are formed with two outer cut surfaces 521 for facilitating the ease of the lower fastening member 50 to be inserted into the drilled hole 73 and for more convenient operation. In the present invention, the number of the outer cut surfaces 521 may be three, four, etc., and will not be further described hereinafter.

Figure 12:
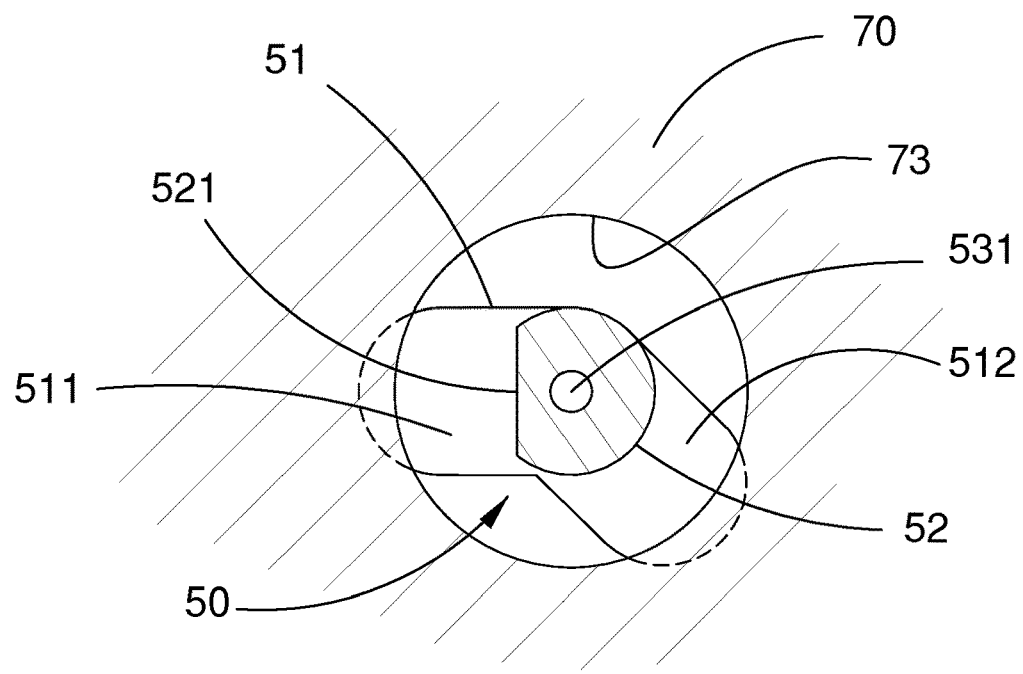
FIG. 12 illustrates a second embodiment of the second base portion of the present invention.
Figure 13:
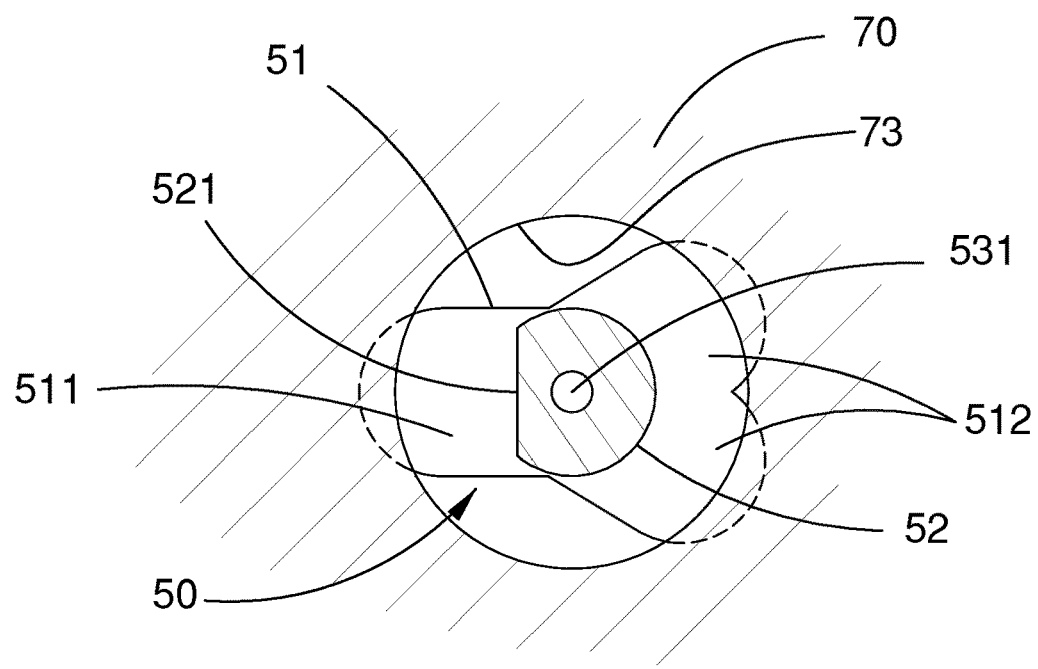
FIG. 13 illustrates a third embodiment of the second base portion of the present invention.

FIG. 12 and FIG. 13 illustrate a second embodiment and a third embodiment of the second base portion 51 of the present invention. The first arm 511 and the second arm 512 of the second base portion 51 of the lower fastening member 50 are connected and arranged at an angle or in a Y shape with the center line Z of the second coupling portion 52 (screw rod) as the center. In the present invention, the first arm 511 and the second arm 512 may be plural in number.

Figure 14:
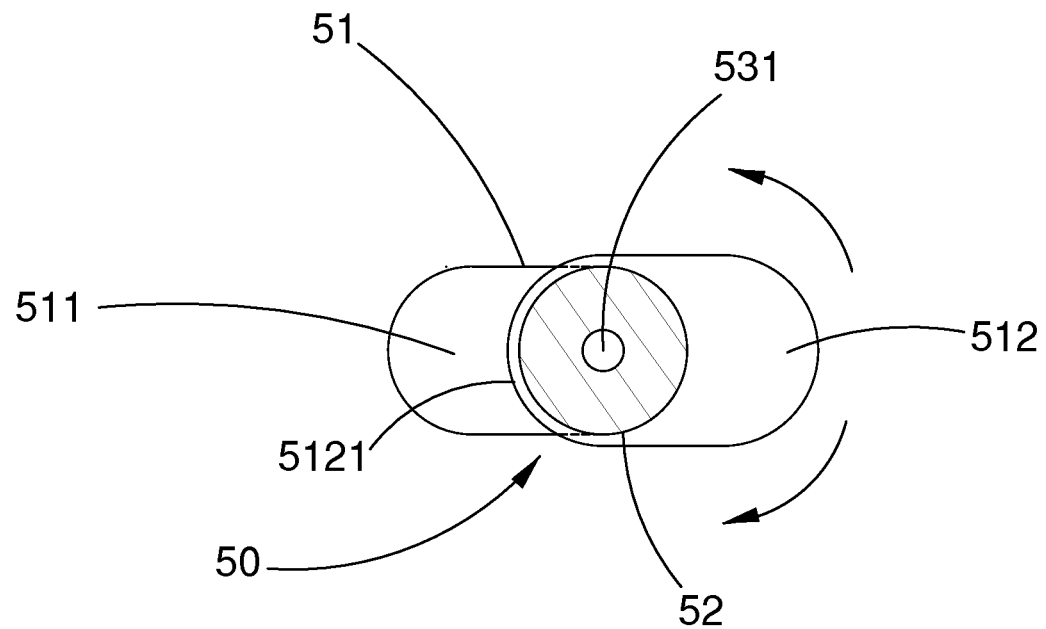
FIG. 14 is a top view of a fourth embodiment of the second base portion of the present invention.
Figure 15:
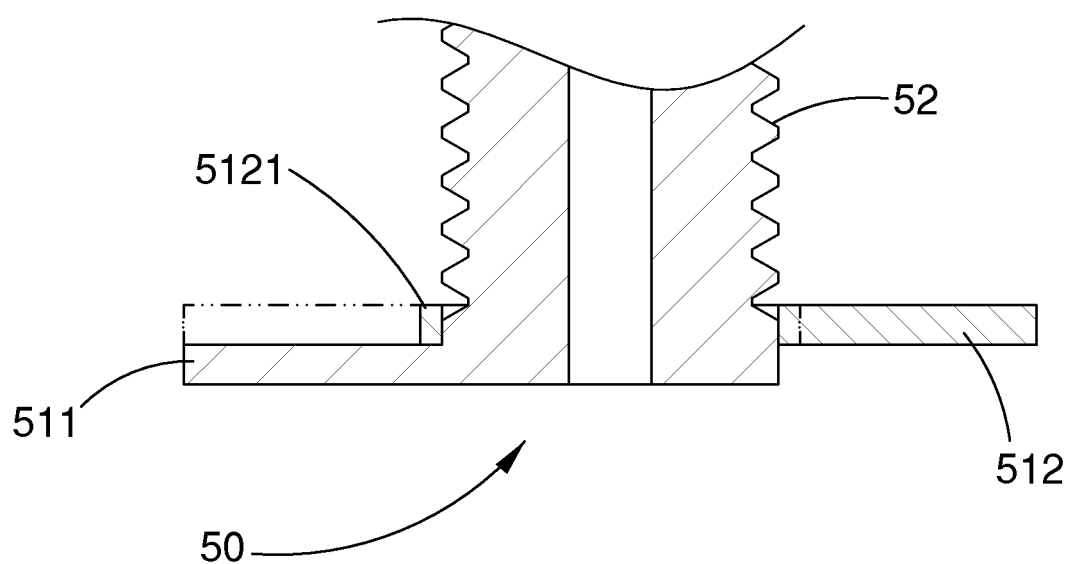
FIG. 15 is an enlarged sectional view of FIG. 14.

FIG. 14 and FIG. 15 illustrate a fourth embodiment of the second base portion 51 of the present invention. The first arm 511 and the second arm 512 are separate elements, that is, the first arm 511 is formed by extending the second coupling portion 52 (screw rod). The second arm 512 has a sleeve portion 5121 fitted onto the second coupling portion 52 (screw rod), so that the second arm 512 is pivotable about the second coupling portion 52 (screw rod). In the present invention, the second arm 512 may be plural in number.

Figure 16:
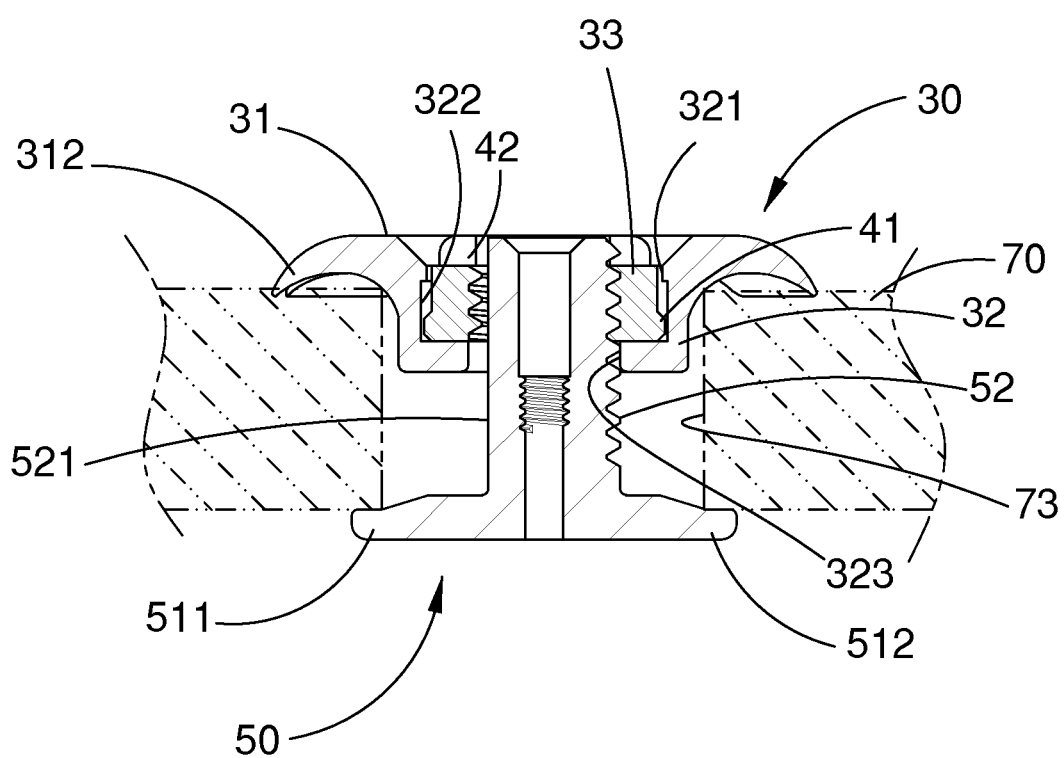
FIG. 16 illustrates a fifth embodiment of the second base portion of the present invention.

FIG. 16 illustrates a fifth embodiment of the second base portion 51 of the present invention. The middle portion of the second base portion 51 (i.e., the root portions of the first arm 511 and the second arm 512) has a larger thickness, thereby not only dispersing the upward pulling force of the second coupling portion 52 but also increasing the structural strength greatly.

The above-mentioned bone drilling cover fixing device A of the present invention is applied to cover a drilled hole 73 of any bone or to fix a cranial bone 72. After the cranial bone 72 is fixed, same as the prior art, the outer sleeve 60 of the surgical tool B is moved upwardly through a reverse rotation so that the surgical tool B is quickly removed from the bone drilling cover fixing device A. Conversely, if the bone drilling cover fixing device A or the cranial bone 72 is to be removed, the bone drilling cover fixing device A can be removed from the cranium (skull) 70 as long as the reverse operation is performed. The present invention is easy and convenient in operation for both implantation and removal.

Figure 17:
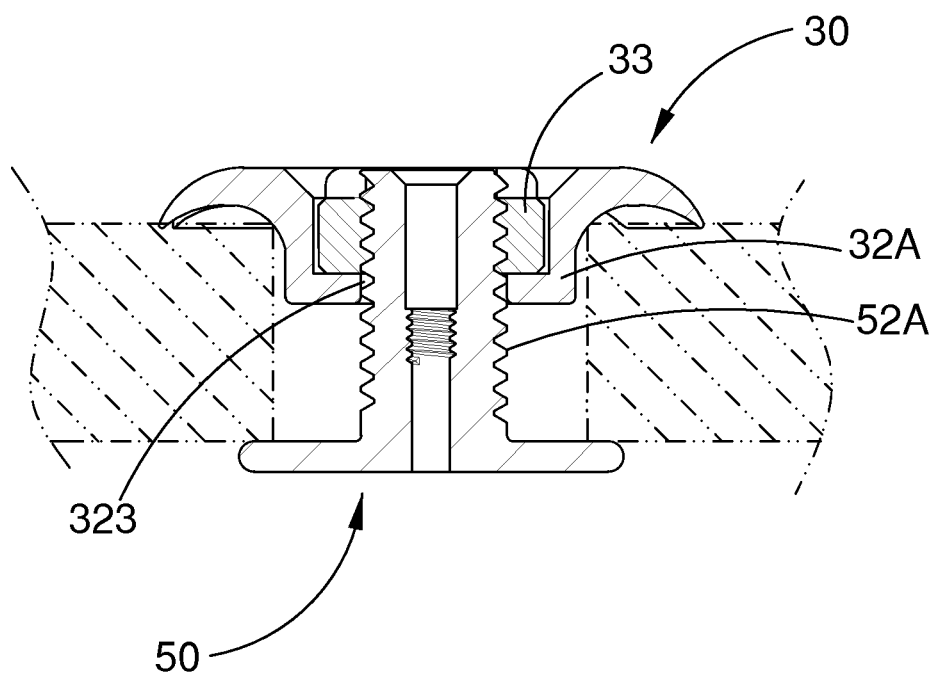
FIG. 17 illustrates a second exemplary combination of the first coupling portion and the second coupling portion of the present invention.

FIG. 17 illustrates a second exemplary combination of the first coupling portion and the second coupling portion of the present invention. The first coupling portion 32A is in the form of an annular sleeve and a nut 33 that are simply fitted, and the second coupling portion 52A is in the form of a screw rod.

Figure 18:
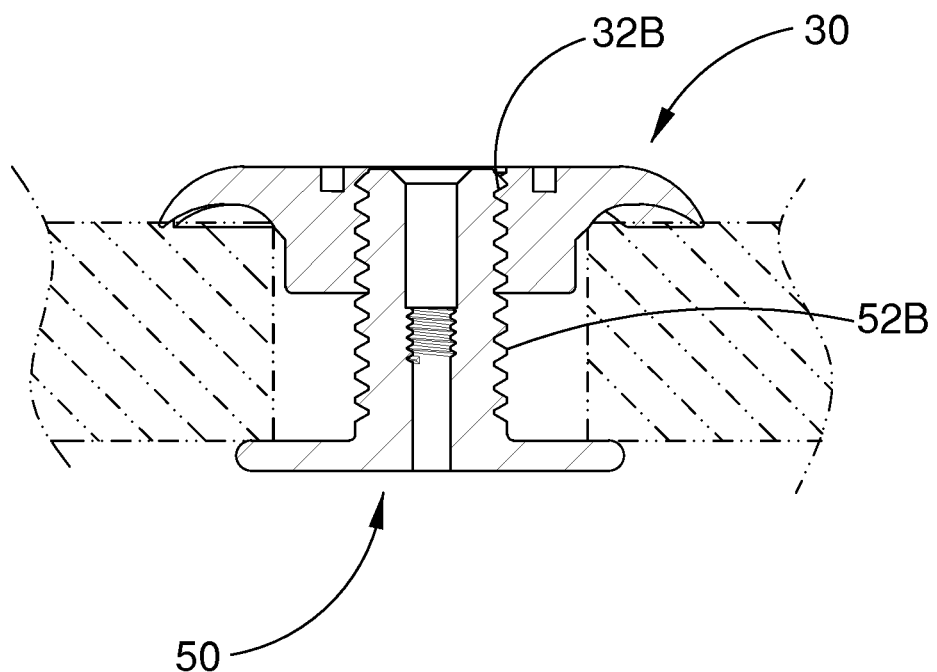
FIG. 18 illustrates a third exemplary combination of the first coupling portion and the second coupling portion of the present invention.

FIG. 18 illustrates a third exemplary combination of the first coupling portion and the second coupling portion of the present invention. The first coupling portion 32B and the second coupling portion 52B are respectively formed with an inner screw hole and a screw rod to be coupled to each other.

Figure 19:
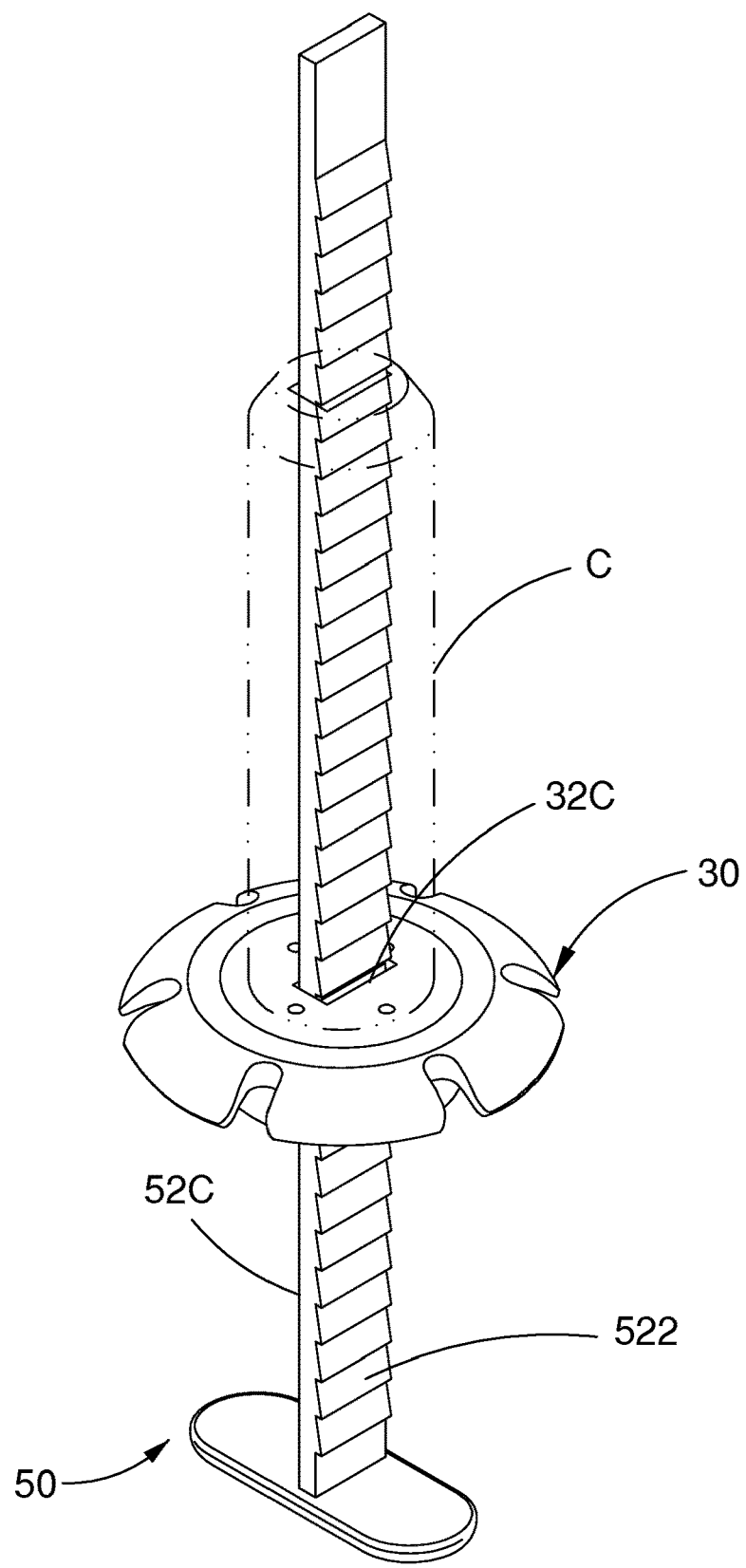
FIG. 19 illustrates a fourth exemplary combination of the first coupling portion and the second coupling portion of the present invention.
Figure 20:
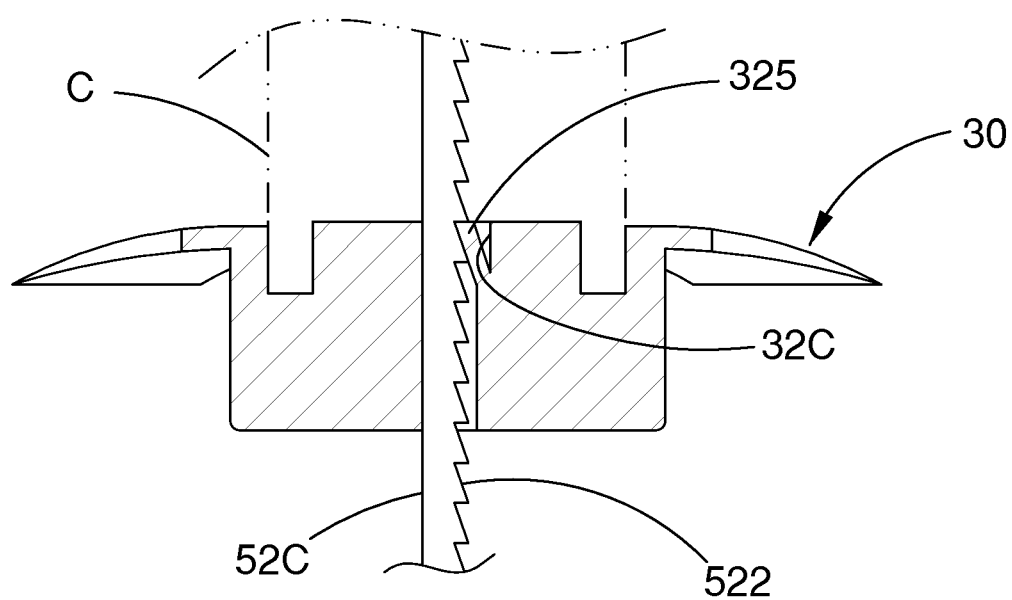
FIG. 20 is a partial sectional view of FIG. 19.

FIG. 19 and FIG. 20 illustrate a fourth exemplary combination of the first coupling portion and the second coupling portion of the present invention, showing a first example of a fastening strip. The first coupling portion 32C is in the form of an engaging hole having a resilient catching portion 325 therein. The second coupling portion 52C is in the form of a long strip having a proper length. At least one side of the strip is provided with a toothed engaging portion 522 that is engagable with the catching portion 325. After the strip is inserted into the engaging hole, the upper fastening member 30 is driven by the surgical tool C to be moved toward the lower fastening member 50 to be tightly fixed for covering the drilled hole.

Figure 21:
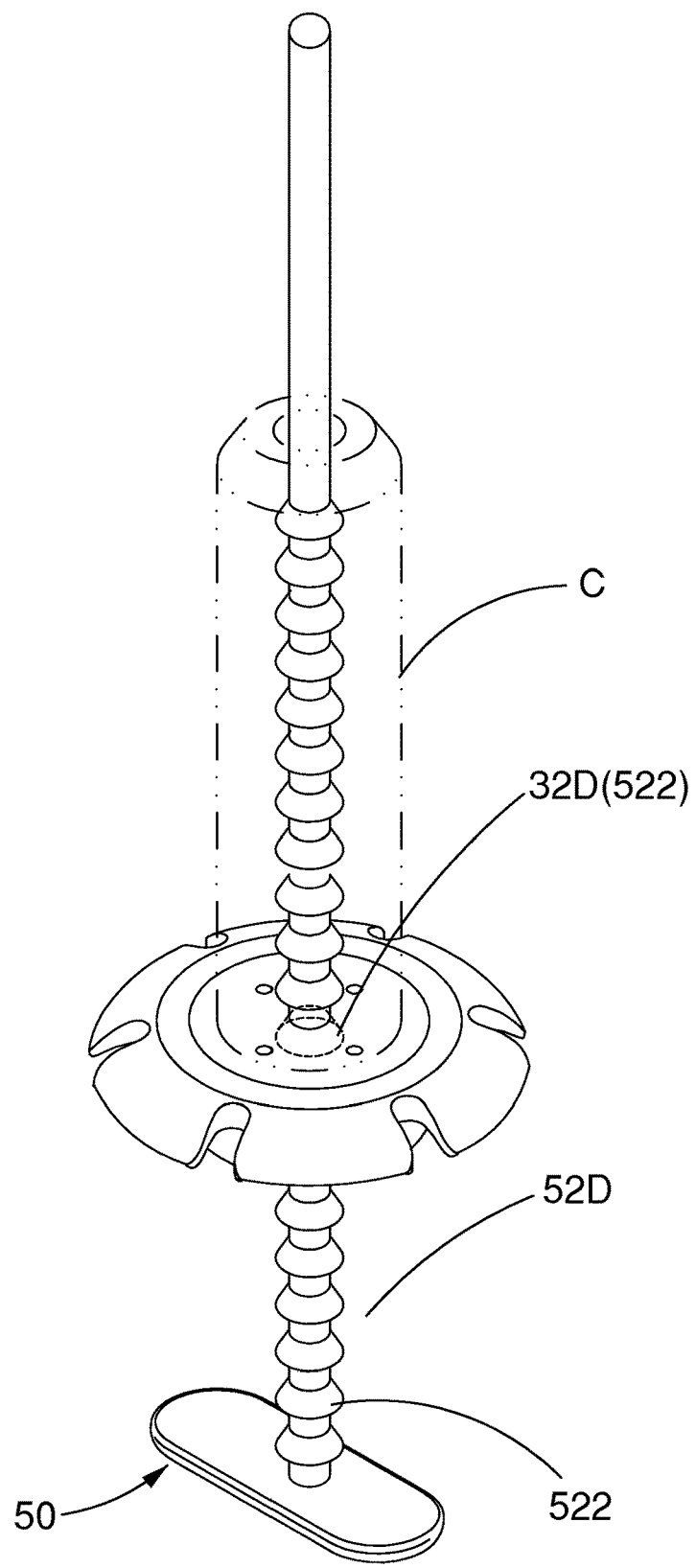
FIG. 21 illustrates a fifth exemplary combination of the first coupling portion and the second coupling portion of the present invention.

FIG. 21 illustrates a fifth exemplary combination of the first coupling portion and the second coupling portion of the present invention, showing a second example of a fastening strip. The first coupling portion 32D is in the form a conical engaging hole that is tapered upwardly. The second coupling portion 52D is in the form of an elongated rod-shaped strip. The rod-shaped strip is provided with a plurality of spaced conical engaging portions 522 that are engagable with the conical engaging hole. After the strip is inserted into the engaging hole, the upper fastening member 30 is driven by the surgical tool C to be moved toward the lower fastening member 50 to be tightly fixed for covering the drilled hole.

Compared with the prior art, the bone drilling cover fixing device A of the present invention provides the following advantages:

1. The first arm 511 and the second arm 512 of the lower fastening member 50 of the invention have the same length that is slightly greater than the radius R1 of the drilled hole 73, and their width is less than the diameter of the drilled hole 73. The lower fastening member 50 is inserted in an oblique manner toward the drilled hole 73, such that the first arm 511 and the second arm 512 can be inserted in an oblique manner and positioned to the underside of the drilled hole 73 for covering the drilled hole 73 of any bone. The operation is very quick and easy. The diameter of the drilled hole 73 is minimized for reducing damage to the bone structure.

2. The invention is aimed at fixing the cranial bone. The first arm 511 and the second arm 512 having the same length are configured to span and hold the cranial bone 72 and the cranium 70 for bone drilling or for fixing the cranial bone to the drilled hole of the any bone. The device can be widely used.

3. The second coupling portion 52 of the lower fastening member 50 of the present invention may be provided with one or two outer cut surfaces 521 corresponding to the side of the first arm 511 or the second arm 512 for facilitating the ease of the lower fastening member 50 to be inserted into the drilled hole 73 and for more convenient operation.

4. In addition to the above-mentioned excellent effects and improvements, the effects of the prior art are also kept, and the functional benefits of the present invention are more enhanced and improved.

In summary, the device of the invention may be used for covering the drilled hole of any bone and for fixing the cranial bone. The operation is easy and quick. The device can be widely used. Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:
1. A bone drilling cover fixing device, comprising:
an upper fastening member, including a first base portion and a first coupling portion, the first coupling portion being disposed on the first base portion and protruding from an underside of the first base portion, the first coupling portion having a diameter less than a diameter of a drilled hole; and a lower fastening member, including a second base portion and a second coupling portion, the second base portion including at least one first arm and at least one second arm, the first arm having a length equal to that of the second arm, the second coupling portion being disposed on the second base portion, each of the length of the first arm and the length of the second arm being greater than a radius of the drilled hole;

wherein, when in use, the first arm and the second arm are inserted in an oblique manner into the drilled hole to be positioned at two ends of an underside of the drilled hole, the second coupling portion is coupled to the first coupling portion, and a movement caused by a clearance between the first coupling portion and the drilled hole is not sufficient to disengage any one of the first arm and the second arm from the two ends of the underside of the drilled hole;

wherein the second base portion is in a platy shape and has a width less than the diameter of the drilled hole.

2. The bone drilling cover fixing device as claimed in claim 1, wherein the first coupling portion and the second coupling portion are a screw hole and a screw rod, respectively.

3. The bone drilling cover fixing device as claimed in claim 1, wherein the first coupling portion is an annular sleeve with a cavity portion having an opening facing upward, a nut is disposed in the cavity portion, the second coupling portion is a screw rod to be screwed to the nut, an upper edge of the cavity portion is formed with an engaging groove having a smaller inner diameter, a raised ring having an outer diameter greater than the engaging groove protrudes from a lower edge of an outer peripheral surface of the nut so that the nut can only rotate axially in the cavity portion without departing from the cavity portion, a first positioning portion is disposed on an upper end of the nut for connecting a surgical tool, and the screw rod is formed with an inner screw hole for connecting the surgical tool.

4. The bone drilling cover fixing device as claimed in claim 1, wherein the second coupling portion has an outer cut surface corresponding to one of the first arm and the second arm.

5. The bone drilling cover fixing device as claimed in claim 1, wherein the second coupling portion has a plurality of outer cut surfaces.

6. The bone drilling cover fixing device as claimed in claim 1, wherein the first arm and the second arm are separate elements that are extendable and retractable and pivotally connected to each other.

7. The bone drilling cover fixing device as claimed in claim 6, wherein the first arm is formed by extending the second coupling portion, and the second arm has a sleeve portion fitted onto the second coupling portion and is pivotable about the second coupling portion.

8. The bone drilling cover fixing device as claimed in claim 1, wherein a middle portion of the second base portion has a larger thickness.

9. The bone drilling cover fixing device as claimed in claim 1, wherein the first coupling portion is an engaging hole, the second coupling portion is an elongated strip, and the strip is provided with an engaging portion that is engagable with the engaging hole.

* * * * *